US010603413B2

(12) United States Patent
Kantrowitz et al.

(10) Patent No.: US 10,603,413 B2
(45) Date of Patent: Mar. 31, 2020

(54) DISINTEGRATING DIGESTIVE TRACT BARRIER

(76) Inventors: Allen B. Kantrowitz, Williamstown, MA (US); Robert D. Fanelli, Pittsfield, MA (US)

( * ) Notice: Subject to any disclaimer, the term of this patent is extended or adjusted under 35 U.S.C. 154(b) by 1871 days.

(21) Appl. No.: 11/560,021

(22) Filed: Nov. 15, 2006

(65) Prior Publication Data

US 2007/0110793 A1    May 17, 2007

Related U.S. Application Data

(60) Provisional application No. 60/736,820, filed on Nov. 15, 2005.

(51) Int. Cl.
| | | |
|---|---|---|
| A61K 38/00 | (2006.01) | |
| A61L 31/14 | (2006.01) | |
| A61L 31/06 | (2006.01) | |
| A61L 31/16 | (2006.01) | |
| A61L 31/18 | (2006.01) | |

(52) U.S. Cl.
CPC ............. *A61L 31/148* (2013.01); *A61L 31/06* (2013.01); *A61L 31/16* (2013.01); *A61L 31/18* (2013.01); *A61L 2300/00* (2013.01)

(58) Field of Classification Search
None
See application file for complete search history.

(56) References Cited

U.S. PATENT DOCUMENTS

| | | | |
|---|---|---|---|
| 3,875,928 A | 4/1975 | Angelchik | |
| 3,983,863 A | 10/1976 | Janke et al. | |
| 4,134,405 A | 1/1979 | Smit | |
| 4,217,890 A | 8/1980 | Owens | |
| 4,315,509 A | 2/1982 | Smit | |
| 4,403,604 A | 9/1983 | Wilkinson et al. | |
| 4,416,267 A | 11/1983 | Garren et al. | |
| 4,501,264 A | 2/1985 | Rockey | |
| 5,306,300 A * | 4/1994 | Berry | 623/23.64 |
| 5,527,337 A * | 6/1996 | Stack et al. | 606/198 |
| 5,786,022 A * | 7/1998 | Agarwal et al. | 427/2.31 |
| 5,957,975 A * | 9/1999 | Lafont et al. | 623/1.16 |
| 6,364,904 B1 * | 4/2002 | Smith | 623/1.22 |
| 6,610,071 B1 * | 8/2003 | Cohn et al. | 606/148 |
| 7,976,461 B2 * | 7/2011 | Ertas | A61B 1/00059 600/101 |
| 2004/0107004 A1 | 6/2004 | Levine et al. | |
| 2004/0117031 A1 * | 6/2004 | Stack et al. | 623/23.65 |
| 2005/0125075 A1 * | 6/2005 | Meade et al. | 623/23.64 |
| 2005/0177181 A1 * | 8/2005 | Kagan et al. | 606/151 |
| 2006/0087442 A1 * | 4/2006 | Smith | G06K 19/06 340/686.1 |

OTHER PUBLICATIONS

Turner et al. in Techniques in Animal Surgery, 2nd Edition, 1989.*
Shea et al. in Journal of Micromechanical Microengineering 5, 297-304, 1995.*
Zhang et al., "Electrostatic micromotor and its reliability," Microelectronics Reliability 45 (2005) 1230-1242.*
Xinli et al., "Advantages of Electrostatic Micromotor and Its Application to Medical Instruments," IEEE (2002), pp. 2466-2468.*

* cited by examiner

*Primary Examiner* — Jared Barsky
(74) *Attorney, Agent, or Firm* — Blue Filament Law PLLC

(57) ABSTRACT

An inventive digestive tract barrier includes a material defining dimensions of a tube sized to deploy within the digestive tract of a subject. The material or stitches that make up the barrier disintegrate in a controlled manner. The disintegration precludes the need for a surgical procedure to retrieve the barrier and allows for increased nutritional absorption after behavior modification has occurred. Through the inclusion of opening or fenestrations in the barrier, bile flow and nutrition absorption are facilitated. Disintegration is facilitated by formation of the barrier from biodegradable material, stitching non-degradable swatches with disintegrating stitching, or the use of a MEMS cutter. A digestive barrier coated on either the interior or exterior of the tube facilitates management of conditions such as obesity, colitis, and Crohn's disease.

16 Claims, 2 Drawing Sheets

DISINTEGRATING DIGESTIVE TRACT BARRIER

CROSS-REFERENCE TO RELATED APPLICATIONS

This application is a non-provisional application that claims priority benefit of U.S. Provisional Application Ser. No. 60/736,820, filed Nov. 15, 2005; the contents of which are hereby incorporated by reference.

FIELD OF THE INVENTION

The present invention in general relates to an intestinal nutrient absorption barrier and in particular to a disintegratable or segmentable barrier.

BACKGROUND OF THE INVENTION

Obesity has reached pandemic proportion in the United States with 55% of adults and 25% of children classified as overweight. Increased meal portion sizes, a sedentary lifestyle, the proliferation of fad diets, and the increased carbohydrate calorie intake associated with low fat diets all contribute to this national health crisis. Some attributes of obesity include: 365,000 deaths per year related to morbid obesity, which is the second leading cause of death in U.S. behind tobacco (435,000 per year); high incidence of depression; higher incidence and poorer prognosis for cancers such as esophageal, prostate, colon, ovarian, cervical, breast, uterine cancer more common; as well as untold physical, economic and psychological impacts.

As obesity progresses, the affected individuals develop medical comorbidities at alarming proportions. These include diabetes mellitus, heart disease, hypertension, dyslipidemia, degenerative joint disease, and numerous others. The five-year death rate among the untreated morbidly obese is over 6%, and this risk is reduced by 89% after successful weight loss surgery has been performed. Diabetes, which affects almost 80% of morbidly obese individuals, is improved in 85% after substantial weight loss and cured in 75%. Coronary artery disease is improved in 45%, hypertension in 55%, and the morbidity and mortality of joint replacement surgery markedly reduced in patients able to achieve meaningful weight loss, typically after weight loss or bariatric surgery.

In extreme cases of morbid obesity that are untreatable through behavioral modification, diet and increased exercise, bariatric surgery is a dangerous final approach to reduce a patient's weight. Weight loss operations vary in aggressiveness, yet share the common feature of reducing or removing the stomach volume with an associated rearrangement of the small intestine to limit the amount of calories both ingested and absorbed. Some procedures solely restrict intake, and are known as restrictive procedures, while others combine restrictive and malabsorptive components to achieve even greater and more sustained weight loss. Unfortunately, the resultant weight loss is invariably accompanied by poor vitamin absorption, a predisposition to malnutrition, and potentially severe or life-threatening metabolic complications. Severe and life-threatening complications may result from surgery because of intestinal leaks from one or more of the intestinal anastomoses, pulmonary complications related to comorbid conditions like sleep apnea, deep venous thrombosis with pulmonary embolism, or postoperative myocardial infarction. Additionally, owing to the radical nature of bariatric surgery, reversal of the procedure upon reaching an optimal weight or suffering intolerable side effects is virtually impossible for many patients.

Another approach to addressing obesity has been the deployment of a gastric and/or intestinal barrier that limits nutrient absorption by creating a physical barrier between the chymal mixture and intestinal epithelial cells. While such barriers have proven effective in reducing subject weight and are reversible through the retrieval of such a barrier, such barriers have met with limited acceptance. Representative barriers are disclosed in U.S. Pat. Nos. 4,134,505; 4,403,604; 4,416,267; and 5,306,300. Safety concerns have developed around these devices associated with barrier dislodgement or kinking, resulting in obstruction or barrier erosion through portions of the gastrointestinal tract resulting in infection, sepsis, and the need for emergency surgery. Additionally, the necessity for a second surgical procedure to safely collapse and retrieve a barrier in response to an intended or emergency retrieval also remains a concern.

Thus, there exists a need for a digestive tract barrier that disintegrates in a controlled manner after deployment. There also exists a need for a variant barrier deployable to treat symptoms of colitis and Crohn's disease.

SUMMARY OF THE INVENTION

A digestive tract barrier is provided that includes a material defining dimensions of a tube, said tube sized to deploy within the digestive tract of a subject. The material or stitches that make up the barrier disintegrate in a controlled manner from a distal end to proximal end relative to a securement that affixes the tube in a preselected position within the subject digestive tract. The disintegration precludes the need for a surgical procedure to retrieve the barrier and allows for increased nutritional absorption after behavior modification has occurred. Through the inclusion of opening or fenestrations in the barrier, bile flow and nutrition absorption are facilitated. Disintegration is facilitated by formation of the barrier from biodegradable material, stitching non-degradable swatches with disintegrating stitching, or the use of a MEMS cutter.

A digestive barrier coated on either the interior or exterior of the tube facilitates management of conditions such as obesity, colitis, and Crohn's disease.

DETAILED DESCRIPTION OF THE PREFERRED EMBODIMENTS

The present invention has utility as a digestive tract barrier that reduces overall digestive tract nutrient absorption from consumed foodstuffs. Indications for the deployment of an inventive barrier include obesity, colitis and Crohn's syndrome.

An inventive barrier is characterized by a securement proximal to a first end, the first end deployed in an upper region of the digestive tract relative to the second end that descends for a predetermined length of intestine. Upon deployment, the barrier defines a bore through which chyme is transported, the barrier wall defining the bore is deployed in contact with the intestinal wall. The inventive digestive barrier inhibits nutrient transportation from the barrier bore to the intestinal wall where food absorption occurs. An inventive barrier is formed from a biodegradable component arrayed such that the lower portion of an inventive barrier, relative to the digestive tract, begins to degrade with the degradation successively moving upward. An inventive barrier by gradually degrading obviates the need for a surgical removal of the barrier and lessens the likelihood of bariatric surgery type side effects such as dumping syndrome. Dumping is an important part of behavioral modification after a gastric bypass; once a patient experiences dumping, behavior is modified to avoid a subsequent episode. With an inventive barrier, dumping is likely to occur at full barrier length, which creates the desired behavior modification even while the barrier thereafter disassembles. As a result, the behavior modification occurs while the likelihood of dumping actually reoccurring diminishes with a shortening barrier. In those subjects prone to develop gallbladder disease, an inventive barrier is optionally deployed that has an inclusion of a porous barrier segment in overlap with the bile duct or alternatively, the deployment of an inventive barrier in an intestinal region lower than the bile duct. While it is appreciated that diversion of the biliopancreatic stream is expected to lessen, the lowered risk of gallbladder disease associated with low motility justifies such a deployment.

Figure 1:
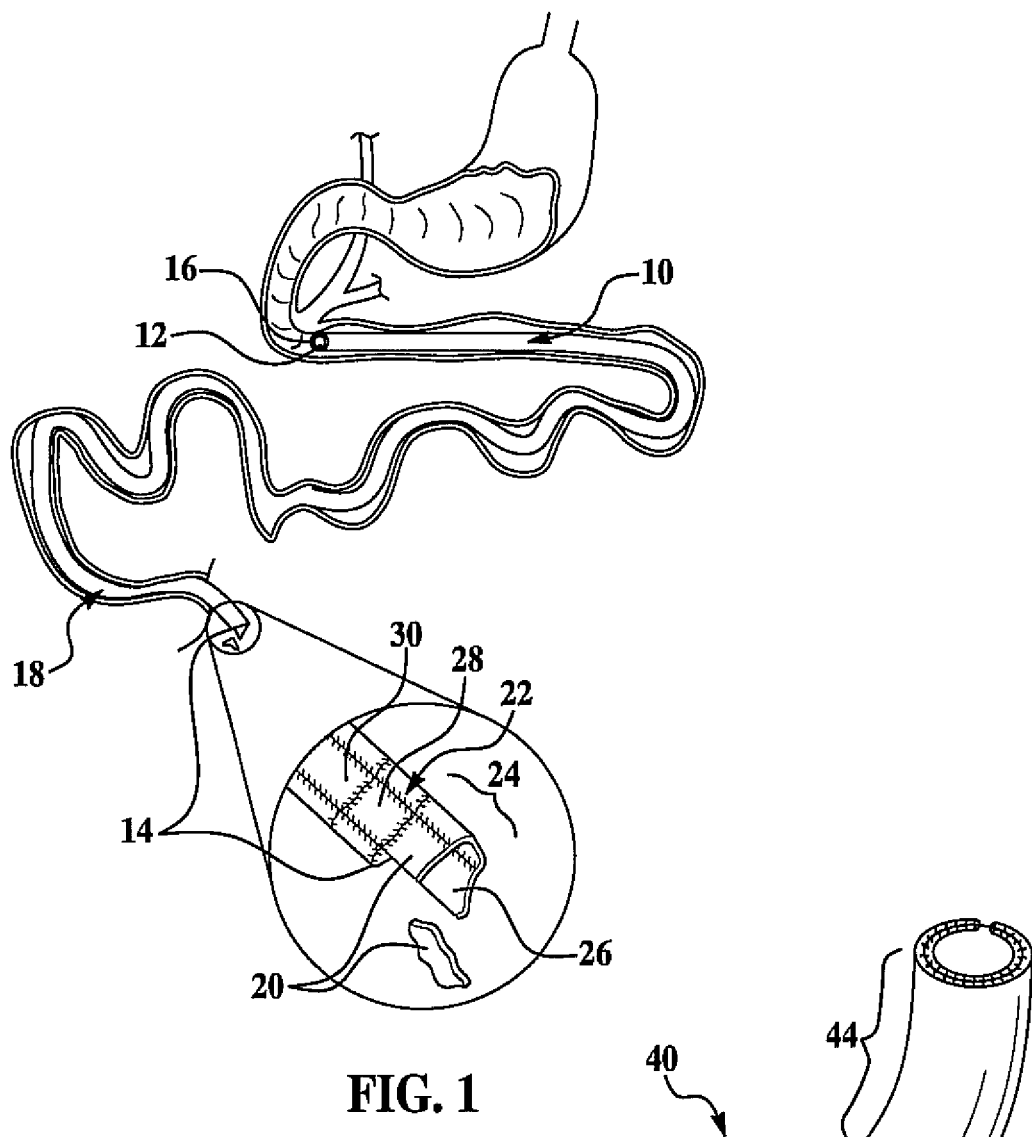
FIG. 1 is a perspective view of an inventive barrier depicted in the context of a human digestive tract; barrier segments are not shown to scale for illustrative purposes.

Referring now to FIG. 1, an inventive barrier is depicted generally at 10. The barrier 10 has an upper end 12 and a lower end 14. A securement 16 is located proximal to the upper end 12 and serves to anchor the barrier 10 while deployed. The nature of the securement 16 is dictated by the criteria of being: collapsible to safely be excreted, and compatible with residence in the digestive tract for a period of time ranging from two weeks to several years. Exemplary securements operative herein illustratively include a tissue adhesive, sutures, and a resilient member biased against surrounding digestive tract tissue. In the embodiment depicted in FIG. 1, the securement 16 engages the duodenum beneath the bile duct so as to promote normal gallbladder motility. The securement 16 is a flexible cartilaginous incomplete ring segment. It is appreciated that a plurality of like securements 16 or a combination of different types of securements are suitable to anchor the upper end 12 of an inventive barrier 10. By way of example, a cartilaginous ring segment may be used in combination with another cartilaginous ring segment, a full cartilage ring, a spring, or a polymerizable tissue adhesive. The tissue adhesive, if present, is in the form of a burstable packet or applied through a multiple bore catheter. The barrier wall 18 extends from the securement to the lower end 14. The barrier wall 18 is composed of multiple swatches 20 of implant-compatible non-degradable fabric or sheet polymer. Suitable materials for a swatch 20 illustratively include nylon, fluoropolymers, and polyimides. The swatches 20 are secured together by way of a stitching 22.

The stitching 22 is in the form of a biodegradable fiber or a scissionable nonbiodegradable fiber. Regardless of the characteristics of the fiber and separation methodology, the inventive barrier is partially removable.

Scission of a nonbiodegradable fiber stitching in the inventive barrier entails deployment of an endoscopic cutting implement to selectively cut portions of the barrier 10 free from the lower end 14. Alternatively, a nonbiodegradable fiber is deployed as stitching that is degraded by ultraviolet light or transient heating. Upon a portion of an inventive barrier being exposed to ultraviolet emissions or transient heating inducing laser light produced by an endoscopic light source, such portion is released from the lower end 14. Ultraviolet light degradable stitching is formed from a polymer, illustratively including cassava starch, poly teralkylmethacrylate cellulose, and lignin. Stitching susceptible to transient heat degradation is formed from a polymer illustrative including polymethacrylates such as alkyl and hydroxyalkyl and polytetrafluoroethylene. In another embodiment nonbiodegradable fiber stitching is selectively scissionable through the deployment of a passive radiofrequency identification (RFID) tag in operative control of a stitch cutter such as an electro-micromechanical microcutter powered by an electrostatically driven harmonic micromotor as detailed in K. S. Shea et al., J. Micromech. Microeng. 5, 297-304 (1994), the contents of which are incorporated by reference as to the construction of a microcutter; a battery-powered IN LED; or a thermoresistive element. In one embodiment a microcutter of Shea, K. S. et al. is used. The Shea cutter is 1 mm or less in length with a diameter of 2 mm. A microcutter is optionally driven by either a single or dual stator mechanism. In one embodiment a cutter is driven by a single stator within a rotor connected to a blade or circular cutting mechanism such as a rotor with a cutting shaft or surrounded by diamond cutting particles. An operable microactuator optionally operates with a rotor radius of about 1020 microns and a stator electrode radius of optionally 1000 microns so as to decrease size and optimize construction. Communicating an activating radiofrequency to the RFID tag engages the stitch cutter positioned proximal to a stitch to cut the stitch thereby releasing a portion of the barrier device. It is appreciated that the deployment of multiple stitch cutters along the length of an inventive barrier, and activated by different radiofrequency signals allows not only a noninvasive method of determining the position and length of the barrier but also a highly controlled truncation method.

Biodegradable polymers operative herein for the formation of fibers, stitches or sheets illustratively include polyglycolic acid, polylactide, polyglyconate, and copolymers thereof. The diameter of a biodegradable fiber from which the stitching 22 is formed increases in cross-sectional area from the lower end 14 to the upper end 12. As the degradation rate and therefore scission time for a stitch 22 increases with an increased diameter for the biodegradable thread from which the stitch 22 is formed, this pattern of stitching induces a generally sequential degradation beginning at the lower end 14. Optionally, the stitching 22 is in the form of a rip stitch or "daisy chain" such that a degradation portion illustratively including a circumference defining series of swatches are released from the end 14 upon a single failure in a stitch 22 within a degradation portion 24. Alternatively, a biodegradable fiber is non-uniformly coated with a semi-permeable diffusion coating that controls the rate of underlying biodegradable fiber degradation. A semi-permeable diffusion coating is formed from materials illustratively including gelatin, cellulose, and polylactic acid.

Optionally, the inner surface, outer surface or both inner and outer surfaces are coated with a biodegradable coating 30. It is appreciated that the coating thickness need not be uniform and by way of example may include a continuous thickness gradient of coating, a discontinuous region of a coating, or a coating application only over a specific barrier component such as a swatch 20 or a stitch 22. A coating 30, if present, optionally includes an adjuvant such as a lubricant; a vitamin; an antimicrobial; an anti-inflammatory; a hormone; an enzyme; a radio-opacifying agent; an appetite suppressant such as hoodia; an appetite stimulant such as Megase; and combinations thereof. Incorporation of an enzyme such as mung bean extracted enzymes is contemplated to convert ingested carbohydrate into non-metabolizable material by the subject. Appetite stimulants are contemplated as particularly beneficial with a short length contact therapeutic device for subjects such as those with malignancy. It is appreciated that incorporating a radio-opacifying agent into a barrier coating facilitates fluoroscopic and x-ray monitoring of barrier placement and condition. Radio-opacifying agents illustratively include barium sulfate and gold nanoparticulate. It is appreciated that coating adjuvants intended to be absorbed through intestinal epithelial cells are present within a coating matrix found on the barrier exterior surface 28. Vitamin B12 is representative of a vitamin typically deficient in a dieting subject and is well suited to intercalation into a barrier coating 30 on the exterior surface 28.

In employment of an inventive barrier 10 in a subject suffering colitis or Crohn's disease, the portion of the inventive barrier contacting inflamed intestinal tissue is formed of a gold mesh or has an exterior coating impregnated with therapeutics such as steroidal or non-steroidal anti-inflammatories, gold, or combinations thereof. The inventive barrier 10 in such a case affords the advantage of continual, contact delivery of therapeutics through diffusion from the barrier coating and depending on the specifics of the therapeutic medicament, at doses higher than deliverable through conventional administration routes. In a particular embodiment, the barrier coating 30 releases metronidazole to inhibit chlamydia proliferation in a subject so infected. A coating 30 on an interior surface in addition to protecting the wall 18 from abrasion, optionally includes adjuvants such as antacids, antioxidants, lubricants and the like.

Figure 2:
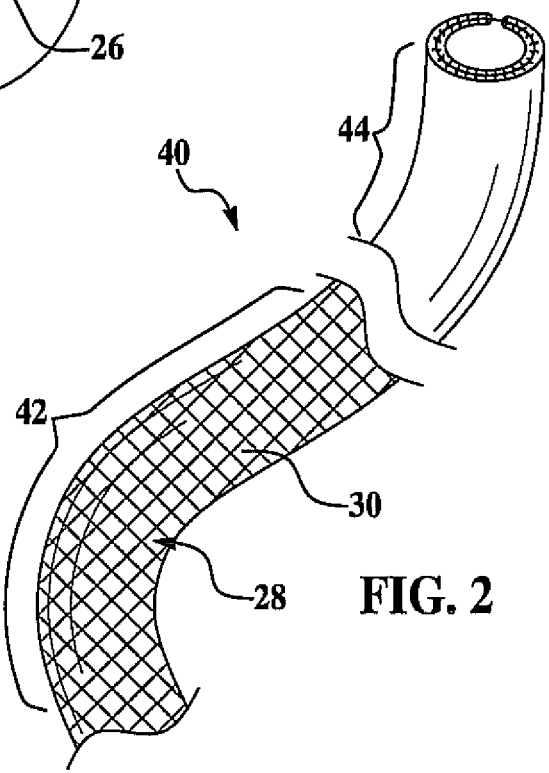
FIG. 2 is a plan view of an inventive barrier having a helical construct having a nutrient transmissive portion.

Referring now to FIG. 2, an inventive barrier is depicted generally at 40 where like numerals correspond to those detailed above with respect to FIG. 1. The barrier 40 is particularly well suited for the treatment of Crohn's disease and is characterized by an impermeable barrier wall portion 42 and an upstream nutrient transmissive portion 44. The nutrient transmissive portion 44 is constructed with fenestrated swatches or only stitch thread extending between the securement 16 and the transmissive portion 44. An inventive barrier 40 preferably includes a coating 30 on the exterior surface 28 of the nutrient impermeable portion 42 of the barrier 40. The coating 30 is preferably impregnated with a diffusible contact therapeutic for the treatment of intestinal inflammation and associated clinical manifestations. Without intending to be bound by a particular theory, it is believed that the barrier 40 provides therapeutic benefits through limiting exposure of inflamed intestinal tissue to digestive tract contents and delivering through contact diffusion suitable therapeutics for the intestinal tissue inflammation.

Figure 3:
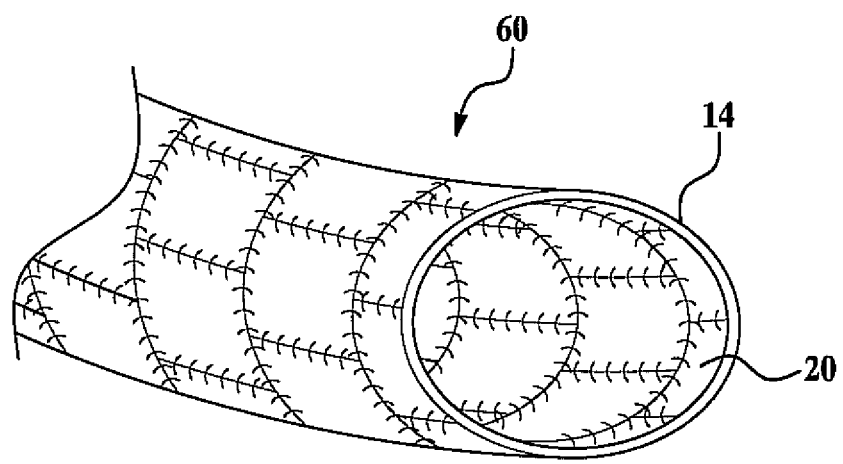
FIG. 3 is an exploded view of an alternate inventive barrier construct portion.

Referring now to FIG. 3, an inventive barrier end with a helical construct pattern is provided generally at 60, where like numerals correspond to those detailed above with respect to FIG. 1. Preferably, the swatches 20 are formed as parallelograms thereby defining helical stitch lines between the intersection of contiguous swatches. Preferably, the stitches 22 securing a particular swatch are self-limiting such that dissolution of a particular stitch is self-limiting and does not cause the entire helix to unravel. Rather, each swatch 20 is sequentially released from the end 14.

Figure 4A:
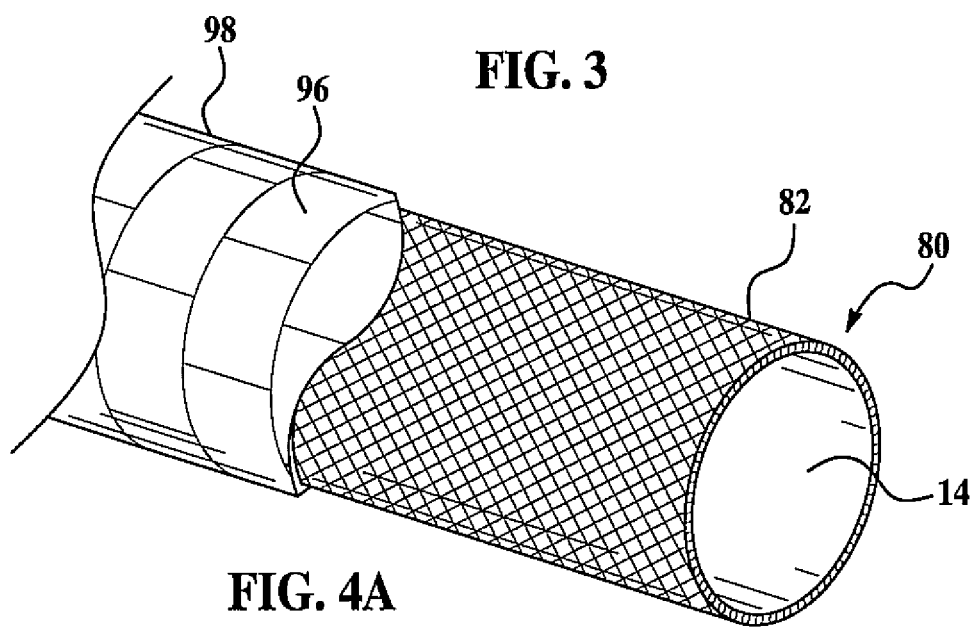
FIGS. 4A and 4B are exploded views of an inventive barrier construct portions formed of biodegradable fiber (A) and sheeting (B).
Figure 4B:
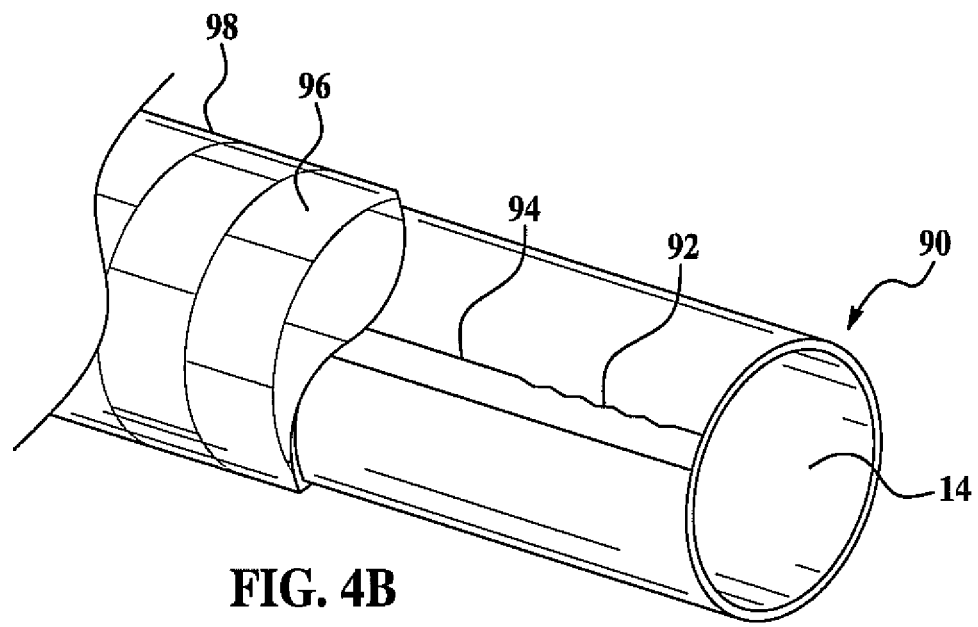

An inventive barrier construction woven of biodegradable fiber is shown generally in FIG. 4A at 80, where like numerals correspond to those detailed above with respect to FIG. 1; and an inventive barrier construction sheet is shown generally in FIG. 4B at 90, where like numerals correspond to those detailed above with respect to FIG. 1. A barrier 80 is formed from biodegradable polymer in the form of fibers 82. The barrier 90 is preferably rolled in the form of a tube and has stitches 92 or is secured with a tissue adhesive 94 as collectively shown in FIG. 4B. The stitches 92 or tissue adhesive 94 are chosen to disintegrate slower than the biodegradable polymer, if at all. Alternatively, a biodegradable material is molded through an extrusion die or injection molded to form a seamless barrier (not shown). The attribute of a gradual disintegration initiating at the lower end 14 and moving up the barrier 80 or 90 is provided by increasing the thickness of the woven fiber or sheet material from the lower end and increasing towards the upper end. Alternatively, a uniform thickness sheeting material or diameter fiber is coated with a semi-permeable encapsulant layer 96 applied in a gradient with the least amount of the semi-permeable layer being present at the lower end. Optionally, a barrier semi-permeable layer coating has a set of score marks 98 in the coating 96 to facilitate coating disintegration into readily excretable particulate. A suitable semi-permeable coating layer is formed from a material illustratively including gelatin, cellulose, and polylactic acid. It is appreciated that adjuvants as detailed above are readily incorporated into a semi-permeable coating.

An inventive barrier is deployed through a variety of techniques conventional to the art. Such techniques include endoscopic deployment, laparoscopic deployment, topo-scopically so as to push the inverted barrier into position, with resort to a guide wire, or in a dehydrated and compressed state. It is appreciated that the compression can be lateral or transverse to the barrier central axis.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A digestive tract barrier having an upper end and a lower end relative to a subject digestive tract comprising:
   a material having dimensions of a tube, said tube sized to deploy within the subject digestive tract, said tube comprising a plurality of material swatches of implant-compatible non-degradable polymer dimensioned such that more than one of said plurality of swatches are joined to define a diameter of the tube;
   a securement affixed to said tube to retain said tube in a preselected position within the subject digestive tract;
   stitching joining said plurality of swatches;
   a stitch cutter adjacent to said stitching; and
   a passive radiofrequency identification (RFID) tag having a RFID frequency in operative control of said stitch cutter.

2. The barrier of claim 1 further comprising a porous segment that is porous towards nutrient exchange with the subject digestive tract.

3. The barrier of claim 1 further comprising a diffusible adjuvant.

4. The barrier of claim 1 further comprising a radio-opacifying agent associated with said securement.

5. The barrier of claim 3 wherein said adjuvant is exterior to the tube.

6. The barrier of claim 3 wherein said adjuvant is palliative towards Crohn's disease or colitis.

7. The barrier of claim 3 wherein said adjuvant is selected from the group consisting of: lubricants, vitamins, antimicrobials, anti-inflammatories, hormones, enzymes, radio-opacifying agents, and combinations thereof.

8. The barrier of claim 1 wherein said cutter is electro-micromechanical microcutter powered by an electrostatically driven harmonic micromotor.

9. A digestive tract barrier having an upper end and a lower end relative to a subject digestive tract comprising:
   a material having dimensions of a tube, said tube sized to deploy within the subject digestive tract, said tube comprising a plurality of material swatches of implant-compatible non-degradable polymer dimensioned such that more than one of said plurality of swatches are joined to define a diameter of the tube;
   a securement affixed to said tube to retain said tube in a preselected position within the subject digestive tract;
   stitching joining said plurality of swatches;
   a first stitch cutter adjacent to a first stitch of said stitching;
   a first passive radiofrequency identification (RFID) tag having a first RFID frequency in operative control of said first stitch cutter;
   a second stitch cutter adjacent to a second stitch of said stitching;
   a second passive radiofrequency identification (RFID) tag having a second RFID frequency in operative control of said second stitch cutter, the second RFID frequency differing from the first RFD frequency.

10. The barrier of claim 9 further comprising a porous segment that is porous towards nutrient exchange with the subject digestive tract.

11. The barrier of claim 9 further comprising a diffusible adjuvant.

12. The barrier of claim 11 wherein said adjuvant is exterior to the tube.

13. The barrier of claim 11 wherein said adjuvant is palliative towards Crohn's disease or colitis.

14. The barrier of claim 11 wherein said adjuvant is selected from the group consisting of: lubricants, vitamins, antimicrobials, anti-inflammatories, hormones, enzymes, radio-opacifying agents, and combinations thereof.

15. The barrier of claim 9 further comprising a radio-opacifying agent associated with said securement.

16. The barrier of claim 11 wherein said first cutter is electro micromechanical microcutter powered by an electrostatically driven harmonic micromotor.

* * * * *